US00PP29459P2

(12) United States Plant Patent
Tuinier

(10) Patent No.: US PP29,459 P2
(45) Date of Patent: Jul. 3, 2018

(54) ***ECHEVERIA* PLANT NAMED 'GREEN DELIGHT'**

(50) Latin Name: ***Echeveria agavoides*×*Echeveria elegans***
Varietal Denomination: Green Delight

(71) Applicant: Wander Durk Tuinier, Krimpen aan den IJssel (NL)

(72) Inventor: Wander Durk Tuinier, Krimpen aan den IJssel (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,824

(22) Filed: Mar. 3, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

(56) References Cited

PUBLICATIONS

PLUTO Plant Variety Database Jan. 20, 2018. p. 1.*

* cited by examiner

*Primary Examiner* — Annette H Para
(74) *Attorney, Agent, or Firm* — C. A. Whealy

(57) ABSTRACT

A new and distinct cultivar of *Echeveria* plant named 'Green Delight', characterized by its flattened rosette growth habit; spatulate pale green-colored leaves; and excellent interiorscape performance.

2 Drawing Sheets

Botanical designation: *Echeveria agavoides*×*Echeveria elegans*.

Cultivar denomination: 'GREEN DELIGHT'.

BACKGROUND OF THE INVENTION

The present invention relates to a new and distinct cultivar of *Echeveria* plant, botanically known as *Echeveria agavoides*×*Echeveria elegans* and hereinafter referred to by the name 'Green Delight'.

The new *Echeveria* plant is a product of a planned breeding program conducted by the Inventor in Krimpen aan den IJssel, The Netherlands. The objective of the breeding program was to develop new and distinct *Echeveria* plants with good interiorscape performance.

The new *Echeveria* plant originated from a cross-pollination made by the Inventor in 2013 of an unidentified selection of *Echeveria agavoides*, not patented, as the female, or seed, parent with *Echeveria elegans* 'Lola', not patented, as the male, or pollen, parent. The new *Echeveria* plant was discovered and selected by the Inventor as a single plant within the progeny of the stated cross-pollination in a controlled greenhouse environment in Krimpen aan den IJssel, The Netherlands.

Asexual reproduction of the new *Echeveria* plant by leaf cuttings in a controlled greenhouse environment in Krimpen aan den IJssel, The Netherlands since September, 2014 has shown that the unique features of this new *Echeveria* plant are stable and reproduced true to type in successive generations.

SUMMARY OF THE INVENTION

Plants of the new *Echeveria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Green Delight'. These characteristics in combination distinguish 'Green Delight' as a new and distinct *Echeveria* plant:

1. Flattened rosette growth habit.
2. Spatulate pale green-colored leaves.
3. Excellent interiorscape performance.

Plants of the new *Echeveria* differ primarily from plants of the female parent selection in the following characteristics:

1. Leaves of plants of the new *Echeveria* are spatulate in shape whereas leaves of plants of the female parent selection are more pointed.
2. Leaves of plants of the new *Echeveria* are more flat than and not as upright as leaves of plants of the female parent selection.
3. Leaves of plants of the new *Echeveria* are thinner than leaves of plants of the female parent selection.

Plants of the new *Echeveria* differ primarily from plants of the male parent, 'Lola', in the following characteristics:

1. Plants of the new *Echeveria* have a less compact rosette form than plants of 'Lola'.
2. Leaves of plants of the new *Echeveria* are longer than and not as round as leaves of plants of 'Lola'.
3. Plants of the new *Echeveria* and 'Lola' differ in leaf color as plants of 'Lola' have pale green-colored leaves that are tinged with pink.

Plants of the new *Echeveria* can be compared to plants of *Echeveria agavoides* 'Red Edge', not patented. Plants of the new *Echeveria* and 'Red Edge' differ primarily in the following characteristics:

1. Plants of the new *Echeveria* are flatter than and not as upright as plants of 'Red Edge'.
2. Leaves of plants of the new *Echeveria* are shorter and more rounded than leaves of plants of 'Red Edge'.
3. Plants of the new *Echeveria* and 'Red Edge' differ in leaf color as leaves of plants of 'Red Edge' are pale green in color with red-colored apices.

BRIEF DESCRIPTION OF THE PHOTOGRAPHS

The accompanying colored photographs illustrate the overall appearance of the new *Echeveria* plant showing the colors as true as it is reasonably possible to obtain in colored reproductions of this type. Colors in the photographs may differ slightly from the color values cited in the detailed botanical description which accurately describe the colors of the new *Echeveria* plant.

The photograph on the first sheet comprises a top perspective view of a typical plant of 'Green Delight' grown in a container.

The photograph on the second sheet is a close-up view of a typical plant of 'Green Delight' grown in a container.

DETAILED BOTANICAL DESCRIPTION

The aforementioned photographs and following observations, measurements and values describe plants grown during the summer in 12-cm containers in a glass-covered greenhouse in Krimpen aan den IJssel, The Netherlands and under cultural practices typical of commercial *Echeveria* production. During the production of the plants, day temperatures ranged from 18° to 25° C. and night temperatures ranged from 12° to 18° C. Plants were 20 weeks old when the photographs and description were taken. In the following description, color references are made to The Royal Horticultural Society Colour Chart, 2015 Edition, except where general terms of ordinary dictionary significance are used.

Botanical classification: *Echeveria agavoides*×*Echeveria elegans* 'Green Delight'.

Parentage:

*Female, or seed, parent*.—Unidentified selection of *Echeveria agavoides*, not patented.

*Male, or pollen, parent*.—*Echeveria elegans* 'Lola', not patented.

Propagation:

*Type*.—By leaf cuttings.

*Time to initiate roots, summer*.—About one week at temperatures about 25° C.

*Time to initiate roots, winter*.—About two weeks at temperatures about 18° C.

*Root description*.—Fine; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial plant; flattened rosette plant form with mostly flat to slightly convex leaves; flattened globular in overall shape; spatulate pale green- colored leaves; low to moderate vigor and growth rate.

*Plant height*.—About 4 cm.

*Plant width*.—About 12.3 cm.

*Interiorscape performance*.—Plants of the new *Echeveria* have excellent interiorscape performance and have been observed to typically survive about one to two years in the interiorscape.

Leaf description:

*Arrangement and quantity*.—Leaves arranged in a basal rosette, simple, generally symmetrical and long-persisting; leaves sessile; about 38 leaves per rosette.

*Leaf length*.—About 5.6 cm.

*Leaf width*.—About 2.8 cm.

*Leaf thickness*.—About 7 mm.

*Leaf shape*.—Spatulate.

*Leaf apex*.—Rounded with a small abruptly acute tip.

*Leaf base*.—Broadly cuneate.

*Leaf margin*.—Entire.

*Leaf aspect*.—Flattened to slightly convex.

*Leaf texture, upper and lower surfaces*.—Smooth, glabrous.

*Leaf luster, upper and lower surfaces*.—Glossy.

*Leaf venation pattern*.—Not visible.

*Leaf color*.—Developing leaves, upper surface: Close to N138C; outer edges, close to 150D. Developing leaves, lower surface: Close to between 191B and 191C; outer edges, close to 150D. Fully expanded leaves, upper and lower surfaces: Close to N138C; outer edges, close to 176C to 176D.

Flower description: Flower initiation and development have not been observed to date on plants of the new *Echeveria*.

Disease & pest resistance: Plants of the new *Echeveria* have not been noted to be resistant to pathogens and pests common to *Echeveria* plants.

Temperature tolerance: Plants of the new *Echeveria* have been observed to tolerate temperatures ranging from about 5° C. to about 40° C. and to be suitable for USDA Hardiness Zones 10 to 12.

It is claimed:

1. A new and distinct *Echeveria* plant named 'Green Delight' as illustrated and described.

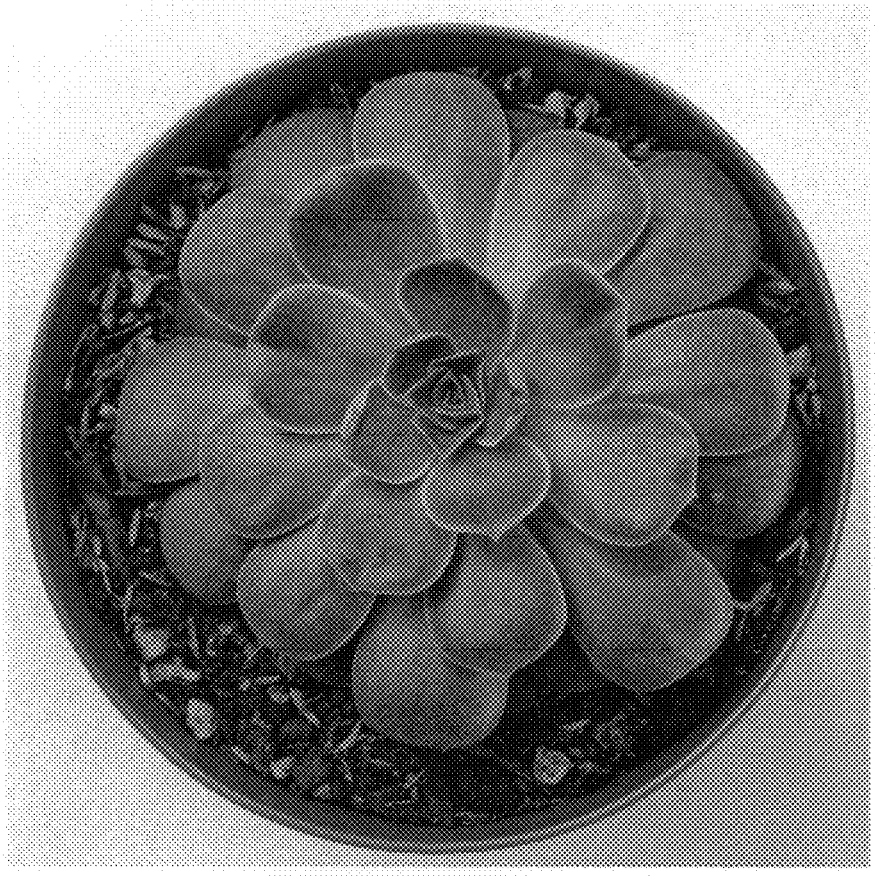

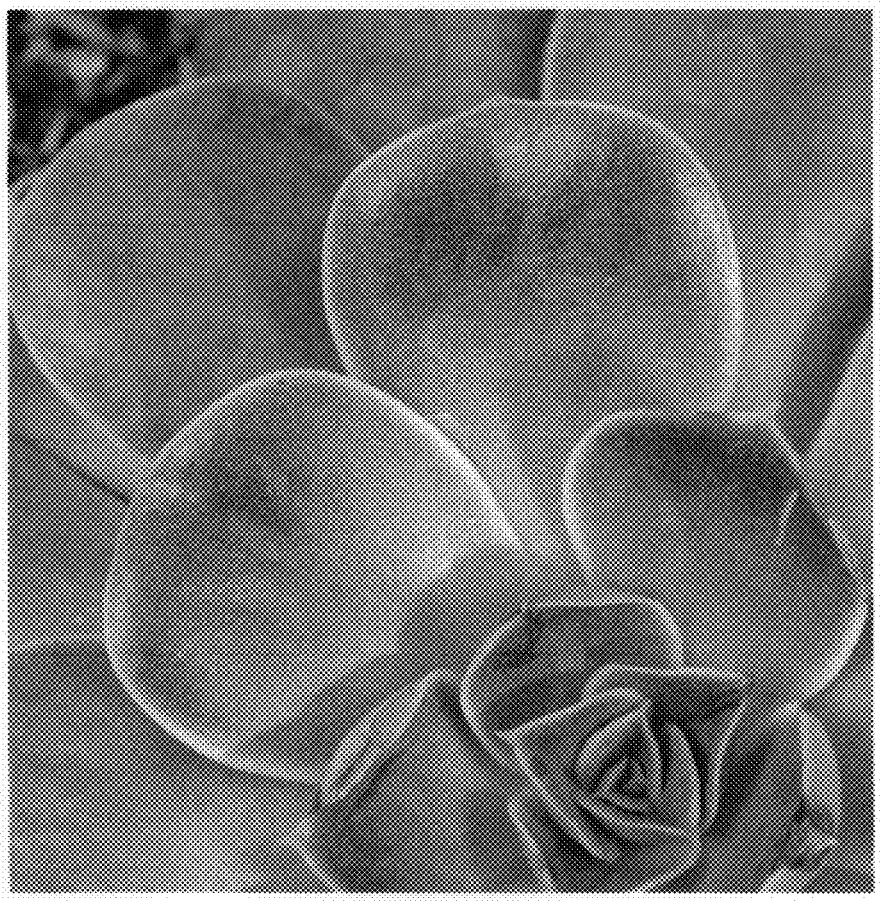

* * * * *